United States Patent [19]

Kent

[11] 4,100,122

[45] Jul. 11, 1978

[54] TRANS-POLYISOPRENE COMPOSITIONS

[75] Inventor: Eric George Kent, Sarnia, Canada

[73] Assignee: Polysar Limited, Sarnia, Canada

[21] Appl. No.: 778,965

[22] Filed: Mar. 18, 1977

Related U.S. Application Data

[63] Continuation of Ser. No. 605,835, Aug. 19, 1975, abandoned.

[30] Foreign Application Priority Data

Sep. 10, 1974 [CA] Canada ..................................209009

[51] Int. Cl.$^2$ .......................... C08K 3/36; C08K 5/01; C08K 7/14
[52] U.S. Cl. ................................ 260/28.5 B; 128/90; 260/42.18; 264/222
[58] Field of Search ........................ 260/28.5 B, 42.18; 264/222; 128/90

[56] References Cited

U.S. PATENT DOCUMENTS

| | | | |
|---|---|---|---|
| 3,490,444 | 1/1970 | Larson | 264/222 |
| 3,656,476 | 4/1972 | Swinney | 128/90 |
| 3,746,669 | 7/1973 | Dunnom et al. | 260/42.18 |

OTHER PUBLICATIONS

Materials and Compounding Ingredients for Rubber, 1975, Bill Communications, Inc., p. 196.

*Primary Examiner*—James H. Derrington
*Attorney, Agent, or Firm*—Stevens, Davis, Miller & Mosher

[57] ABSTRACT

Trans-polyisoprene composition of improved dimensional stability and stiffness are prepared by blending trans-polyisoprene with glass fibres and reinforcing silica. A crystalline wax may also be added to the compositions, to provide easier moldability.

7 Claims, No Drawings

TRANS-POLYISOPRENE COMPOSITIONS

This is a Continuation of application Ser. No. 605,835 filed Aug. 19, 1975, now abandoned.

This invention relates to trans-polyisoprene compositions, more particularly to trans-polyisoprene compositions containing inorganic reinforcing materials.

Trans-polyisoprene is a well known thermoplastic rubbery material, produced commercially by the polymerization of isoprene with a catalyst chosen so as to direct the polymerization towards the production of polymer with the units thereof linked predominantly in the trans-1,4 configuration. Trans-polyisoprene is essentially a synthetic balata, and is used in a number of applications where natural balata is also used, e.g. as a golf ball covering material.

The thermoplastic nature of trans-polyisoprene allows it to be readily molded into various shapes, and permits its use in applications where ease of molding and remolding is required. In addition however, trans-polyisoprene has a low softening point, so that it can be softened and shaped at relatively low temperatures, so low in fact that it can be molded onto and hardened in contact with human skin without causing discomfort. This property, plus the stiffness of the cool, molded material, had led to the use of trans-polyisoprene and compositions based thereon in medical casts, used to immobilize a fractured limb, and for orthopaedic puposes. For these purposes a sheet of trans-polyisoprene composition can be softened in hot water, applied around the limb whilst soft, and cooled in situ around the limb to form the cast.

However, there are problems associated with the use of known trans-polyisoprene compositions in thermoplastic areas. A particular such problem is a slight lack of rigidity exhibited by thin sections of trans-polyisoprene compositions such as sheets. Trans-polyisoprene also exhibits a degree of "rubberiness" that makes it unsuitable for certain industrial applications.

A further difficulty preventing a wider use of trans-polyisoprene compositions and exploitation of their advantageous properties lies in a lack of absolute retention of dimensional stability. When a molded sample of trans-polyisoprene is heated to or near its softening temperature, it tends to distort somewhat from its molded shape.

It is an object of the present invention to provide a trans-polyisoprene composition which reduces one or more of the aforementioned disadvantages.

It has now been found that trans-polyisoprene compositions of improved dimensional stability and stiffness can be prepared by blending trans-polyisoprene with glass fibres, and with a finely divided reinforcing silica.

Thus according to the present invention, there is provided a thermoplastic, remoldable composition comprising a mixture of trans-polyisoprene, short chopped glass fibres and a finely divided reinforcing silica filler.

By the term "trans-polyisoprene" as used herein is meant a high molecular weight polymer of isoprene having a trans-1,4 content of at least 85%, a crystallinity as determined by x-ray diffraction of about 15–40%, and a Mooney viscosity (ML-4 at 100° C) of about 5 to 50. The crystalline melting point of such a trans-1,4-polyisoprene is from about 20° to about 80° C.

Preferably, compositions according to the present invention comprise a mixture of 100 parts by weight trans-polyisoprene, from about 5 to about 50 parts by weight of short chopped glass fibres and from about 5 to about 40 parts by weight of a finely divided reinforcing silica filler.

It has been found that the inclusion of glass fibres, in combination with silica fillers, in trans-polyisoprene compositions significantly increases the flexural modulus and flexural strength of the resulting compositions, and a significantly increases their dimensional stability.

The glass fibres which may be blended with the transpolyisoprene according to the present invention can have a length of from about ¼ inch to about 1/64 inch, and a diameter from about 2 to about 50 microns. The fibres so used are produced by milling in a hammer mill and are preferably chopped to an average length of about 1/32 inch, the short length avoiding any interference with the molding characteristics of the transpolyisoprene. Preferred diameters of the fibers are from about 4 to about 25 microns. If desired, the glass fibres may be coated with chemicals such as silanes, in order to improve the adhesion of the glass fibres to the trans-polyisoprene. Preferred quantities of glass fibres are from 10 to 40 parts by weight per 100 parts by weight of trans-polyisoprene.

The finely divided reinforcing silica filler which may be blended with trans-polyisoprene in accordance with the present invention can be used in amounts varying from about J to about 40 parts by weight of silica filler per 100 parts by weight of trans-polyisoprene. The silica fillers used are those commonly used as reinforcing agents for rubbers, i.e. the fine particle size (about 10 to about 200 millimicrons) materials which may or may not be surface treated. In a preferred embodiment, the silica filler is used in an amount of from about 30 to about 40 parts by weight per 100 parts by weight of trans-polyisoprene.

According to a further embodiment of the present invention, there is provided a composition comprising a mixture of transpoly-isoprene, short chopped glass fibres, finely divided reinforcing silica filler and a crystalline wax. The presence of crystalline wax in the compositions modifies the physical properties thereof, and provides easier moldability of the compositions, so that more intricate shapes can be molded from them. Suitably, the amount of crystalline wax is from about 5 to about 50 parts by weight, preferably 15 to 30 parts by weight, per 100 parts by weight of trans-polyisoprene in the composition.

The crystalline wax which can be used in this invention may be a natural wax of vegetable or animal origin, a petroleum wax or a synthetic wax, having a melting point of at least 40° C, preferably from about 50° to about 100° C, and most preferably from about 50° to about 65° C. Representative such natural waxes are beeswax, chinese wax, shellac spermacetti wax, candelila, Carnauba, Palmer Wax, sugar cane wax, Japan wax, Ouricuri wax, ceresin, monatan wax or ozocerite. Synthetic waxes include solid esters of polyhydric alcohols, e.g. stearates of glycerine, hydrogenated castor oil, high molecular weight (C18–30) acids or alcohols, and paraffin waxes such as produced in the Fischer-Tropsch process. When it is desirable to have a composition for manual handling which becomes rubbery at moderate temperatures of up to about 60° C, the low melting waxes are preferably used. In applications such as tubing and films, which are normally exposed to higher operating temperatures, the higher melting waxes are preferable. For specific applications, it may be desirable to mix a high melting wax with a low melting wax or a natural wax with a synthetic wax or a paraffin wax with an ester of a polyhydric alcohol so as to adjust the melting point of the mixture or to make the wax more or less compatible with the polymer. Complete compatibility is not desired as it would affect the crystallization of the wax-polymer composition, leading to changes in the hardness and stiffness of the resulting composition.

It is also desirable to include, in the compositions of the present invention, small amounts of clay fillers. The presence of clay assists in the molding of the material, in addition to increasing the bulk of the compositions as a whole. The clays to be used are known as hard clays; hard clays have a specific gravity of above about 2.4, preferably of the order of 2.6, and have at least 85%, preferably 87–97%, of the particles of less than 2 micron size. Suitably, the amount of clay included is from about 0 to about 40 parts by weight, and preferably from 5 to 25 parts by weight, of clay per 100 parts by weight of trans-polyisoprene. In addition, the compounds of the present invention may contain conventional ingredients normally found in trans-polyisoprene compositions, such as pigments, (titanium dioxide and the like), antioxidants, etc.

Mixtures of trans-polyisoprene and reinforcing silica filler are known and have been used for medical casts and orthopaedic and prosthetic devices. Glass fibres have been incorporated into many plastic materials in order to improve the strength thereof. In the present invention, it has been discovered that the presence of both of reinforcing silica filler and short chopped glass fibres in trans-polyisoprene compositions leads to an entirely unexpected apparently synergistic effect as evidenced by quite remarkable improvements in the flexurable strength and the flexural modulus of such compositions. The addition of a crystalline wax to such compositions appears to improve the flow characteristics of the compositions during their preparation thereby giving a better dispersion of the glass fibres and obtaining the fullest benefit due to the presence of the silica filler and glass fibres. The further addition of a hard clay reduces the cost of the compositions without detracting from their high strength properties.

The method of preparing the compositions of the present invention is not critical, provided that an intimate admixture of all of the various ingredients is achieved. The ingredients may be mixed together in a banbury, on a mill, in the presence or absence of liquid mixing aides and lubricants, etc.

Medical casts or prosthetic/orthopaedic devices are prepared from these compositions by methods already well known in the art by heating sheets of the composition to a temperature not exceeding about 75° C thereby to soften the composition, allowing the softened sheet to cool to a temperature which permits direct contact with the patient's skin, usually about 40° to 50° C, molding the sheet around the area to be supported and to the desired configuration and allowing the molded composition to harden in its molded configuration. Any imperfection in the molding can be corrected by warming, with hot water or a hot air gun, at the point to be corrected followed by the necessary remolding.

Specific preferred embodiments of the invention are illustrated in the following specific examples.

EXAMPLE 1–8.

A series of compositions were prepared containing trans-polyisoprene in admixture with various amounts of chopped glass fibres and various amounts of finely divided reinforcing silica (Hisil-trademark). The compositions were prepared by mixing the ingredients together in a banbury at a temperature of 93° C, which is above the crystalline melting point of the trans-polyisoprene. Then the compositions were sheeted out, cooled and tested for flexural strength and flexural modulus, in accordance with ASTM Procedure D-790-66, method A.

Prior to testing, the samples were conditioned by being maintained in air at a temperature controlled at $23 \pm 2°$ C and at a relative humdity controlled at $45 \pm 5\%$. Then the samples were tested according to the above ASTM method. The test specimens were each 12.5 cm long, 1.27 cm wide and about 0.64 cm thick. The test involves supporting the test sample bar on a simple beam on two supports and applying a load by means of a loading nose midway between the supports. The specimen is deflected until it passes the yield point. Duplicate specimens are tested, and the two results averaged. The load applied to cause yield is the flexural yield strength, and is expressed in kilograms per sq. cm. The flexural modulus (or tangent modulus of elasticity) is the ratio within the elastic limit of the stress to corresponding strain. It is calculated from the tangent drawn to the steepest initial straight line portion of the load-deformation curve. It is expressed in kilograms per sq. cm.

The compositions used and results obtained are given in Table 1. The chopped glass fibres used in all of the compositions had an average length of 1/32 inch, in each case. All of the compositions included 5 parts by weight of titanium dioxide as a pigment, and 1 part by weight of an antioxidant, namely DEENAX (trademark), which is 2,6-ditertiary butyl-4-methylphenol (available from ENJAY Chemical Company).

Examples 1 and 6 are controls containing, respectively, no glass fibres and no silica filler. The low strength properties of these compositions are readily apparent. Examples 2 to 5 and 7 and 8 clearly demonstrate the significant improvements which are achieved in flexural strength and flexural modulus when both the glass fibre and the silica filler are present in the compositions.

TABLE 1

| Example No. | 1 | 2 | 3 | 4 | 5 | 6 | 7 | 8 |
|---|---|---|---|---|---|---|---|---|
| Trans-polyisoprene (parts by weight) | 100 | 100 | 100 | 100 | 100 | 100 | 100 | 100 |
| Chopped glass fibres (parts by weight) | — | 5 | 10 | 25 | 35 | 10 | 10 | 20 |
| HISIL (reinforcing silica) (parts by weight) | 15 | 15 | 15 | 15 | 15 | — | 40 | 30 |
| Titanium dioxide (parts by weight) | 5 | 5 | 5 | 5 | 5 | 5 | 5 | 5 |
| DEENAX antioxidant (parts by weight) | 1 | 1 | 1 | 1 | 1 | 1 | 1 | 1 |
| Flexural strength Kg/cm² | 120 | 136 | 140 | 151 | 162 | 91 | 174 | 167 |
| Flexural modulus | | | | | | | | |

TABLE 1-continued

| Example No. | 1 | 2 | 3 | 4 | 5 | 6 | 7 | 8 |
|---|---|---|---|---|---|---|---|---|
| Kg/cm² | 2915 | 3670 | 4480 | 5940 | 7370 | 2370 | 6875 | 5265 |

EXAMPLE 9–12

Operating in accordance with Examples 1–8, a series of compositions was prepared containing trans-polyisoprene, chopped glass fibres, reinforcing silica, wax, and clay. The wax used was a crystalline petroleum wax of melting point 125° F, available under the trademark PARAWAX. The clay used was a finely divided mineral clay available under the trademark SUPREX, which is a hard clay having a specific gravity of 2.6 and 87–97% of the particles being less than 2 micron size. The compositions were made and tested as described in connection with the previous examples. The compositions prepared and the results obtained are given in Table 2.

Example 9 is a control containing no glass fibres and showing that the presence of only the other components in the composition does not impart high strength. Example 12 shows that compositions containing trans-polyisoprene, glass fibres, silica filler and wax have improved properties in comparison to the controls.

TABLE 2

| Example No. | 9 | 10 | 11 | 12 |
|---|---|---|---|---|
| Trans-polyisoprene (parts by weight) | 100 | 100 | 100 | 100 |
| Chopped glass fibres (parts by weight) | — | 40 | 40 | 40 |
| HISIL (parts by weight) | 80 | 40 | 40 | 40 |
| PARAWAX (parts by weight) | 20 | 20 | 25 | 50 |
| SUPREX Clay (parts by weight) | 10 | 10 | 10 | — |
| Titanium dioxide (parts by weight) | 5 | — | — | — |
| DEENAX (parts by weight) | 1 | — | — | — |
| Flexural strength (kg/cm²) | 44 | 125 | 143 | 114 |
| Flexural modulus (Kg/cm²) | 2000 | 5200 | 7390 | 6410 |

The compositions of the present invention are useful in applications where remoldable thermoplastic rubbery materials of relatively high rigidity are required. In particular, the compositions are useful for making medical casts for the immobilization of the body and limbs, and their increased rigidity renders them suitable for lower extremity medical splinting.

What is claimed is:

1. A thermoplastic remoldable composition of improved dimensional stability and stiffness comprising a mixture of 100 parts by weight of trans-1,4-poly-isoprene, 5 to 50 parts by weight of short, chopped glass fibres and 5 to 40 parts by weight of finely divided reinforcing silica filler, wherein said trans-1,4-polyisoprene is a high molecular weight polymer of isoprene having a trans-1,4 content of at least 85%, a crystallinity as determined by X-ray diffraction of about 15–40%, a Mooney viscosity (ML-4 at 100° C) of about 5 to 50 and a crystalline melting point of from about 20° C to about 80° C.

2. The composition of claim 1 wherein the silica filler has a particle size of 10 to 200 millimicrons.

3. The composition of claim 1 wherein the glass fibres have a length of 1/64 inch to ¼ inch and a diameter of 2 to 50 microns.

4. The composition of claim 1 which also contains from 5 to 50 parts by weight of a crystalline wax having a melting point of at least 40° C.

5. The composition of claim 4 wherein the melting point of the crystalline wax is from 50° to 100° C.

6. The composition of claim 4 which also contains from 5 to 25 parts by weight of a hard clay.

7. The composition of claim 6 wherein the hard clay has a specific gravity of greater than 2.4 and at least 85% of particles of less than 2 micron size.

* * * * *